United States Patent [19]
Chase et al.

[11] Patent Number: 5,840,253
[45] Date of Patent: Nov. 24, 1998

[54] CELL WASH APPARATUS

[75] Inventors: Eric Chase, Walnut Creek; Harvey Schulte, Los Altos; Howard L. North, Los Gatos, all of Calif.

[73] Assignee: Cytek Development Inc, Fremont, Calif.

[21] Appl. No.: 667,449

[22] Filed: Jun. 20, 1996

[51] Int. Cl.⁶ .............................. G01N 21/00; B01L 3/02; B01L 11/00; B01L 9/00
[52] U.S. Cl. ............................ 422/63; 422/100; 422/101; 422/104; 494/41; 494/38; 494/64; 494/16
[58] Field of Search ....................... 435/2, 287.3; 494/41, 494/38, 64, 16, 17, 18; 422/63, 100, 101, 106

[56] References Cited

U.S. PATENT DOCUMENTS 4,058,252  11/1977  Williams ..................................... 233/14
5,215,376  6/1993  Schulte et al. ........................... 366/348

*Primary Examiner*—Lynette F. Smith
*Assistant Examiner*—Brett Nelson
*Attorney, Agent, or Firm*—James P. Hillman

[57] ABSTRACT

An apparatus and method are disclosed to wash blood cells in a discrete manner that is compatible with automated sample preparation systems. The test tube containing the cells to be washed is mounted on a rotatable spindle. The spindle includes central passageways for the introduction of wash fluid and air into the test tube, and radial exit passageways at the bottom of the spindle. The test tube is first spun about its vertical axis to centrifuge cells against the inner wall of the test tube. A vacuum is then applied to the exit passageways so cell supernatant is aspirated out through the exit passageways. Wash fluid is then introduced into the test tube, and aspirated out through the exit passageways, thereby washing the cells. Rotational acceleration and deceleration of the test tube then resuspends the cells in wash fluid.

10 Claims, 3 Drawing Sheets

CELL WASH APPARATUS

FIELD OF THE INVENTION

This invention relates to a method and apparatus for washing biological cells that is compatible with automated equipment.

BACKGROUND OF THE INVENTION

Many procedures involving the preparation of biological cells for analysis require that unreacted reagents and cellular debris be separated from the cells of interest. Traditionally batch centrifugation has been the method of choice to perform this separation. However, batch centrifugation is not readily adaptable to automated sample preparation systems. Most automated sample preparation equipment utilize circular or rectangular arrays of disposable test tubes. The test tubes are transported to appropriate positions so various operations can be performed sequentially and discretely on each test tube. In many sample preparation procedures, the time between discrete operations must be carefully controlled to obtain reliable and reproducible results. However, the operation of cell washing by centrifugation, as it is practiced in the art, is a batch operation. This batch operation cannot be performed sequentially and discretely on each test tube. The presence of a batch operation by definition disrupts the timing of the discrete operations which precede and follow the batch operation.

Batch centrifugations require substantially equal volumes of liquid in each tube to balance the centrifuge rotor, which may not always be desirable in an automated sample preparation sytem. Batch centrifugations require rotational alignment of the centrifuge rotor with the loading/unloading system which introduces additional complexity into the centrifuge drive. Samples also require positive sample identification after centrifugation to verify rotational alignment was achieved. Lastly, the centrifuge rotor and loading/unloading apparatus increases the size, weight and complexity of the system.

In spite of these limitations, automated sample handling systems that utilize batch centrifugation do exist. The ASHS system, marketed by Automed, automates the loading and unloading of conventional centrifuges using robotics; however such systems are large and costly, and only suitable for high volume laboratories.

Another category of instruments has been developed for blood washing and processing, as described in U.S. Pat. Nos. 5,405,308, 4,983,158, 4,668,214, 4,300,717, and 4,086,924. Generally these instruments consist of a a bowl assembly with a central feed tube to introduce blood or wash solution to the bowl, feed tube and seal assembly which provide an input feed line to the bowl and an output line from the bowl, and a core assembly that inparts angular velocity to the incoming fluid. These instruments are not suitable for cell washing in automated sample preparation equipment because they require specialized bowl/core structures to enhance the processing of large quantities (ca 500 ml) of undiluted blood.

A number of companies market automatic cell washers. One such system, the Centra-W Automatic Cell Washer marketed by IEC, automate the aspiration of supernatant and addition of diluent, but still require manual loading and unloading of the sample containers into and from the centrifuge rotor. Consequently, these types of instruments are not compatible with automated sample preparation equipment.

It would be desirable to have a method and apparatus to wash cells that are compatible with automated sample preparation equipment. Such a method and apparatus should operate on each sample individually so it can be synchronized with the other discrete operations performed on the samples. It would also be desirable to have an apparatus that could be implemented as a discrete processing station on the periphery of a carousel or linear track sample preparation system. Furthermore, it would be desirable to perform the wash step in the same disposable test tubes commonly used in automated sample preparation and analysis equipment. It would also be desirable for the cell washer to effectively wash out the undesired cellular debris and unreacted reagents, and to concentrate the desired cells. Lastly, it would be desirable to have the cell washer apparatus operate without an elaborate system to transport the sample containers to and from the cell washing apparatus.

SUMMARY OF THE INVENTION

The invention described herein provides an improved apparatus and method for removing debris and unbound reagents from cellular suspensions contained in disposable test tubes. The cell washer invention can be implemented into a variety of sample processing systems by a variety of suitable handling system embodiments familiar to those skilled in the art.

A disposable test tube containing the cell suspension to be washed is rotated about its longitudinal center line at speeds sufficient to force the cell suspension up the inner wall of the test tube. This film, typically less than a millimeter thick, is retained by an O-ring near the end of a spindle assembly concentric with the test tube. The O-ring also transfers torque from the spindle to the test tube to rotate it. After a few seconds of rotation, the larger, more dense cells will migrate radially to the inner wall of the test tube under the action of centrifugal forces. At this time, a cell compatible washing fluid is delivered to the bottom of the test tube from an external reservoir. This wash fluid displaces the fluid containing smaller and less dense cells, cellular debris, and unbound reagent upwards, through radial passageways in the spindle, and out through suitable passages to an external waste reservoir. Wash fluid thus displaces and removes the unwanted supernatant cell suspension fluid and thus effects a washing of the cells. This process continues until the desired degree of cell washing is achieved. The wash fluid and waste fluids may be moved by suitable pumps which may produce a vacuum inside of the test tube. In the preferred embodiment described a pump producing a vacuum is used because it is a simple system and allows easy introduction and removal of air and washing fluid. The annular outflow passage in the spindle assembly has an outer diameter which in conjunction with the test tube inner diameter establishes the radial thickness of the cell suspension fluid. Thus each final washed cell suspension has the same fixed fluid volume. The initial cell suspension fluid volume may be greater than the final washed cell suspension volume without loss of cells to waste. After the cells are adequately washed, the wash fluid flow is stopped. Then the drive motor is rapidly stopped by braking, either mechanically or electrically. Dynamic braking of a permanent magnet field direct current motor is used in the preferred embodiment because it is simple, convenient, and does not add parts which can wear out. The rapid stopping of the test tube rotation causes the fluid inside the test tube to continue rotating which washes over the cells at the test tube inner wall, which in turn resuspends the cells. Not all cells may be resuspended by a single rapid stopping of the test tube rotation, so the test tube may be rotated and stopped several times to increase cell recoveries. Also, the use of a cell compatible surfactant may be used in the wash fluid to inhibit cell sticking to the test tube. At this point, cell washing and suspension are complete. Vacuum inside the test tube is released, and the spindle is disengaged from the test tube. The cell washer is then ready for engagement with the next test tube for washing.

DESCRIPTION OF PREFERRED EMBODIMENTS

Figure 1:
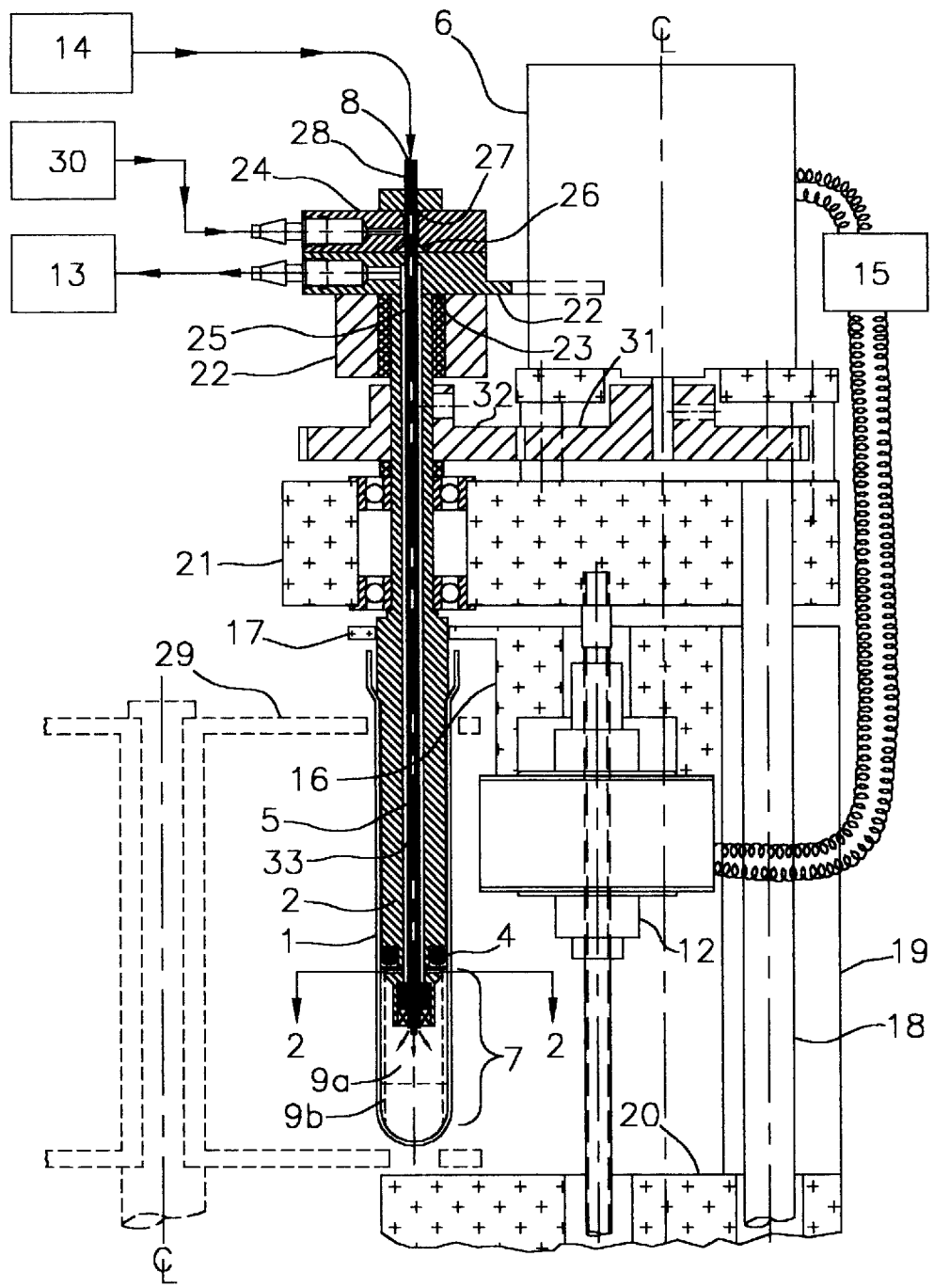
FIG. 1 is a cross sectional view of the cell washer, showing a test tube mounted on the apparatus.

Referring to FIG. 1, the cell washing cycle begins when the carousel 29 brings test tube 1 containing a cell suspension to be washed into position directly below cell washer spindle 2. Control system 15 then causes spindle 2 to be lowered by actuator 12. Spindle support 21 and guide rods 18 in guide housing 19 couple the linear motion of actuator 12 to spindle 2. Spindle 2 is lowered such that O-ring 4 makes sealing contact with the inner wall of test tube 1, and the end of spindle 2 is at the desired height above the bottom of test tube 1. By virtue of the friction between O-ring 4 and test tube 1, actuator 12 lifts test tube 1 a small distance out of carousel 29. Control system 15 then causes motor 6 to rotate spindle 2 and test tube 1 via gears 31 and 32 at a speed such that the cell suspension rapidly forms an annular cylinder of liquid with an inner diameter located at 9a. O-ring 4 prevents the cell suspension from travelling further up the inner wall of test tube 1.

Test tube 1 is rotated for a period of time such that the larger, more dense cells in the suspension are brought into contact with the inner wall of test tube 1, but unreacted reagents and most of the smaller, less dense cells and cellular debris remains within the annular cylinder of liquid 7 with inner diameter at 9a.

Figure 2:
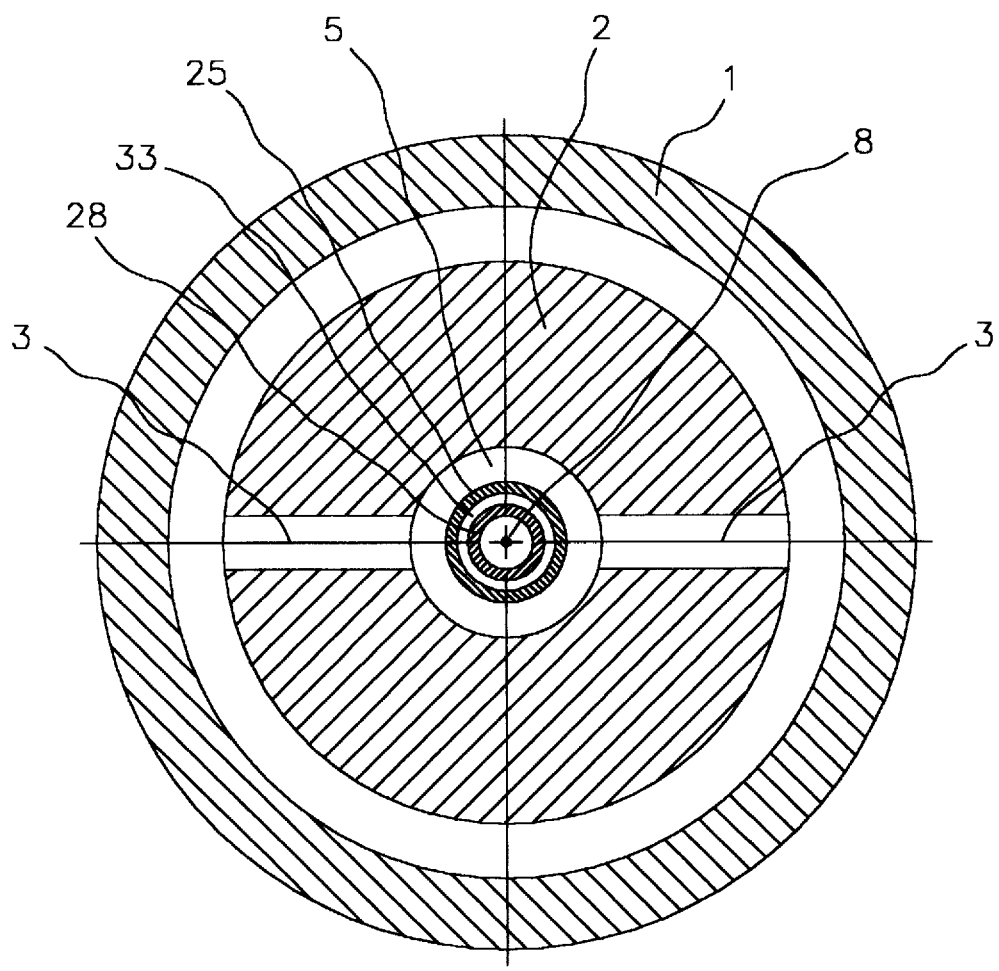
FIG. 2 is a cross sectional view along line 2—2 of FIG. 1.
Figure 3:
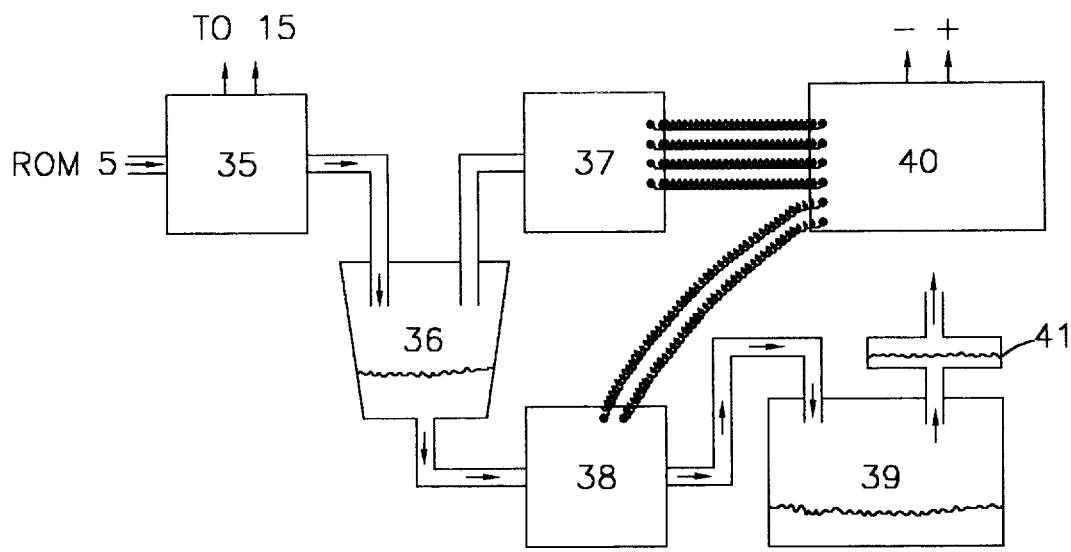
FIG. 3 illustrates the vacuum system of the present invention. This Figure is an expanded view of item 13 shown in FIG. 1.

Normally closed solenoid valve 35 of FIG. 3 is then energized by control system 15 to connect vacuum to the interior of test tube 1 via effluent conduit 5 and effluent passageways 3. Liquid containing smaller, less dense cells, cellular debris and unreacted reagents is pulled through effluent passageways 3, up through effluent conduit 5, to vacuum accumulator 36, through vacuum pump 38, and out to waste reservoir 39. As shown in FIG. 2, effluent conduit 5 is formed by the inner diameter of rotating spindle 2, and the outer diameter of the non-rotating vent conduit tube 25. Effluent face seal 23 seals the top of rotating spindle 2 to the non-rotating effluent housing 22.

Figure 5:
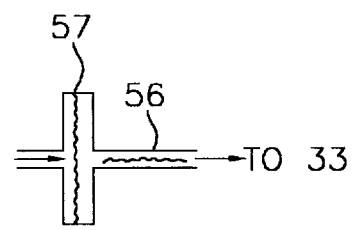
FIG. 5 illustrates the air supply system of the present invention. This Figure is an expanded view of item 30 shown in FIG. 1.

Air passes though filter 57 and flow resistor 56 of FIG. 5, though vent housing 24, and down to the interior of test tube through vent conduit 33. As shown in FIG. 2, vent conduit 33 is defined by the inner diameter of non-rotating vent conduit tube 25, and by the outer diameter of non-rotating wash tube conduit 28. The vent conduit tube 25 is supported at its discharge end by bearing 10 and sealed by seal 11 in spindle 2. Vent conduit 33 is sealed against atmosphere by upper vent conduit seal 27, and lower vent conduit seal 26. The air flowing through vent conduit 33 replaces the liquid pulled from test tube 1 via vacuum system 13. Liquid flows from test tube 1 through effluent conduit 5 until the inner diameter of the annular cylinder of liquid moves from 9a to 9b. At this point, vacuum system 13 begins to pull air provided by vent conduit 33, through effluent passageways 3, the air is then pulled into effluent conduit 5 and from there to vacuum accumulator 36 and finally to waste reservoir 39. Since there is very little pressure drop in effluent passageways 3 and effluent conduit 5, the vacuum in test tube 1 approaches the value in the vacuum accumulator 36. The annular volume defined by diameter 9b is typically half of the volume defined by diameter 9a, which will result in a desirable doubling of cell concentration in the washed suspension compared to the initial unwashed suspension.

Figure 4:
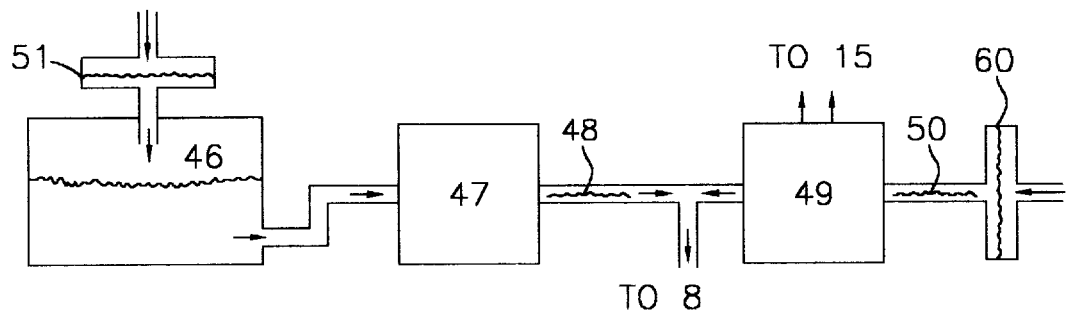
FIG. 4 illustrates the wash fluid supply system of the present invention. This Figure is an expanded view of item 14 shown in FIG. 1.

While the test tube 1 is rotating, and after the annular volume in test tube 1 has been reduced to that defined by diameter 9b, solenoid valve 47 of FIG. 4 is opened by control system 15 while solenoid valve 35 of FIG. 3 remains opened so that wash fluid is drawn by vacuum pump 38 from wash fluid reservoir 46, through wash fluid conduit 8, and into test tube 1. The wash fluid flows in virtually a solid stream from the lower tip of wash fluid conduit tube 28 to the bottom of test tube 1. The inner diameter 9b of the annular cylinder of liquid moves slightly toward the center of test tube 1 due to the addition of wash fluid. When effluent passageways 3 become blocked by the inward movement of the liquid, air flowing into test tube 1 through vent conduit 33 raises the pressure within test tube 1, while the vacuum within effluent conduit 5 remains substantially constant. This creates a pressure differential across effluent passageways 3. When sufficient pressure differential is created across effluent passageways 3 to overcome the pressure created by centrifugal force on the liquid in effluent passagesays 3, the liquid flows out through effluent conduit 5. Air provided by air supply 30 thus purges passageways 3 and effluent conduit 5 of liquid, and the vacuum within test tube 1 again increases. The inner diameter 9b of the annular cylinder of liquid again decreases due to the inflow of wash fluid. This cycle is repeated as long as wash fluid is being supplied by wash fluid conduit 8, vacuum is being applied to effulent conduit 5, and air flows via vent conduit 33. The volume of liquid removed in each cycle and the length of each cycle is dependent on the size of flow resistor 48, the size of flow resistor 56, the vacuum level in vacuum accumulator 36, and the rotational speed of spindle 2. To control the vacuum level in vacuum accumulator 36, vacuum sensor 37 senses the vacuum in the vacuum accumulator 36. The vacuum control electronics 40 compares the vacuum in the vacuum accumulator 36 to a preset reference level, and controls the power provided to vacuum pump 38 to maintain the desired vacuum. It is desirable to limit the volume of liquid associated with each cycle to a few percent of the volume of the annular volume of liquid defined by diameter 9b in order to provide an exact and reproducible volume of liquid remaining in test tube 1 at the end of the wash cycle.

The dilution of unbound reagent by the present invention is not limited by the size of the test tube, whereas the dilution of unbound reagent by conventional centrifugation is limited by the size of the test tube. In the present invention, fluid containing unbound reagent is displaced by the wash fluid, and a laminar flow velocity profile is established within liquid annulus 7 with zero velocity at the test tube wall, and maximum upward velocity at the inner diameter of the annulus 9b. In the absence of diffusion and mixing, the only unbound reagent remaining after a wash cycle is contained within a wedge shaped annulus whose lower width is zero, and whose upper width is defined by the distance between the inner wall of test tube 1 and the circle at which the upward velocity is just sufficient to reach effluent passageways 3 during the wash cycle. For example, if the initial cell suspension is 1.0 ml, the final cell suspension is 0.5 ml, wash fluid is supplied at 1.0 ml/sec for 15 sec, the height of annulus 7 is 2.0 cm, and the diameter of test tube 1 is 1.0 cm, the average upward velocity of fluid will be 4.0 cm/sec. At a point 0.00125 cm from the test tube wall, the velocity will be 0.13 cm/sec, which is the minimum velocity required to reach the effluent passageways during the wash cycle. The volume of fluid contained in this wedge shaped annulus is 0.0039 ml, hence the dilution of the unbound reagent by the present invention is 120×, and the cell concentration factor is 2×. With conventional centrifugation, with the same 1.0 ml initial and 0.5 ml final volumes, and assuming a remaining volume of 0.1 ml of liquid after centrifugation and removal of supernatant, the dilution is only 5× and the cell concentration factor is 2×.

After sufficient wash time has elapsed, solenoid valve 47 of FIG. 4 is closed, and the wash fluid flow is halted. Solenoid valve 49 is then opened briefly to allow air to enter test tube 1 through filter 60, flow resistor 50, and wash fluid conduit 8 in order to purge wash fluid conduit 8 of wash fluid. Motor 6 is then rapidly stopped by system controller 15. Since fluid annulus 7 continues to rotate relative to the test tube wall, cells at the wall of test tube 1 are flushed from the wall and are thereby resuspended. A suitable surfactant in the wash fluid may reduce the adherence of cells to the interior wall of test tube 1, and aid in the resuspension of cells. In addition, motor 6 may then be rapidly accelerated and decelerated one or more times to more completely remove cells from the the inner wall of test tube 1. The motor 6 is then stopped, solenoid valve 35 is closed. Actuator 12, then raises spindle 2 via spindle support 21. As the spindle 2 is being raised, retaining member 17 holds test tube 1 down, to separate it from the spindle 2. Before spindle 2 is completely removed from test tube 1, the spindle may be rotated at a low speed to remove any liquid which may be adhering to the bottom end of the spindle. This will promote more fluid and cell recovery and reduce sample carryover effects. After spindle 2 is fully disengaged from test tube 1, carousel 29 is rotated to bring another test tube into position for cell washing.

We claim:

1. Apparatus for washing cell suspensions within a test tube having an inside surface and an axis of symmetry, comprising:
   a) a frame;
   b) stopper means rotatably disposed on said frame for frictionally engaging said test tube's inside surface sufficient to rotate said test tube;
   c) rotating means for rotating said stopper means and said test tube about said axis of symmetry;
   d) washing means positioned within said stopper means for both adding a wash solution to said cell suspension in said test tube and removing excess wash solution and waste from said cell suspension in said test tube during rotation of said test tube about said axis.

2. The apparatus of claim 1 wherein said axis is vertical.

3. The apparatus of claim 1 wherein the apparatus is adapted for having the test tube presented to said apparatus in a carousel or rack and wherein said apparatus further includes an insertion and removal means for inserting and withdrawing said stopper means into and out of said test tube when said test tube is so presented.

4. The apparatus of claim 3, wherein said insertion and removal means further includes a retaining member for restraining the test tube in its position when the insertion and removal means is withdrawing the stopper means out of the test tube.

5. The apparatus of claim 4 wherein said insertion and removal means includes a linear actuator drive and a guide disposed on the frame for providing vertical movement of said frame to provide for inserting and removing the stopper means into and out of said test tube.

6. The apparatus of claim 1 wherein said stopper means further includes an O-ring disposed in an O-ring seat on the periphery of said stopper means to provide for frictional gripping of said test tube inside surface sufficient for support and rotation of said test tube.

7. The apparatus of claim 6 wherein said stopper means includes a rotatable spindle assembly means for rotating said stopper means and said supported test tube, said rotatable spindle assembly means having an inner diameter annular wall, and wherein said washing means includes a wash solution introduction and removal means, said wash solution introduction and removal means including two co-axial tubes disposed in said spindle assembly forming one circular and two annular conduits, a first fixed inner wash fluid input tube forming a circular wash solution input conduit for conducting wash solution through said stopper into said test tube, a second intermediate fixed vent tube concentric to said inner wash fluid input tube provides an annular vent conduit for conducting a controllable flow of air though said stopper into said test tube, and a third annular outer waste evacuation conduit having a fixed inner wall of said vent tube and wherein the inner diameter of said rotatable spindle assembly provides a rotatable outer wall.

8. The apparatus of claim 7 wherein said spindle assembly means includes exit passageways located at a predetermined outside diameter of said spindle assembly means such that when said test tube is rotated and vacuum is applied to said exit passageways, excess wash fluid, which may contain biological waste, flows out through said exit passageways and a fixed reproducible volume of wash fluid containing said cell suspension is retained in a cylindrical annulus located between and defined by the inner wall diameter of said test tube and said predetermined outside diameter of said spindle assembly means where said exit passageways are located, said third annular outer waste evacuation conduit being in fluid communication with said exit passageways in order to remove excess wash and biological waste liquid from said test tube.

9. The apparatus of claim 8 further including a vacuum means placed in fluid communication with said third annular outer waste evacuation conduit of said wash solution introduction and removal means to remove said wash solution from the test tube to an external reservoir and to create a vacuum within the test tube causing wash solution to be drawn into the test tube through said wash solution input wherein said annular vent conduit provides a controllable flow of air into said test tube and out through said wash solution removal conduit to aid the flow of liquid through said exit passageways.

10. The apparatus of claim 9 wherein said spindle assembly means further includes a spindle bearing and seal assembly disposed between said second intermediate fixed vent tube and said spindle assembly means rotatable inner diameter annular wall to support and locate said second intermediate fixed vent tube.

* * * * *